United States Patent
Hall et al.

(10) Patent No.: US 7,211,082 B2
(45) Date of Patent: May 1, 2007

(54) MAGNETICALLY NAVIGABLE TELESCOPING CATHETER AND METHOD OF NAVIGATING TELESCOPING CATHETER

(75) Inventors: Andrew F. Hall, St. Charles, MO (US); Walter M. Blume, Webster Groves, MO (US)

(73) Assignee: Stereotaxis, Inc., St. Louis, MO (US)

( * ) Notice: Subject to any disclaimer, the term of this patent is extended or adjusted under 35 U.S.C. 154(b) by 416 days.

(21) Appl. No.: 10/774,550

(22) Filed: Feb. 9, 2004

(65) Prior Publication Data
US 2004/0158142 A1    Aug. 12, 2004

Related U.S. Application Data

(63) Continuation of application No. 09/999,185, filed on Feb. 4, 2002, now abandoned, which is a continuation of application No. 09/393,521, filed on Sep. 10, 1999, now Pat. No. 6,385,472.

(51) Int. Cl.
*A61B 18/18* (2006.01)
*A61B 5/04* (2006.01)

(52) U.S. Cl. .................. 606/41; 604/95.04; 600/374; 600/585

(58) Field of Classification Search .............. 606/41, 606/48–50; 604/95.04, 95.05; 600/585, 600/374; 607/122
See application file for complete search history.

(56) References Cited

U.S. PATENT DOCUMENTS

| | | | |
|---|---|---|---|
| 3,674,014 A | 7/1972 | Tillander | |
| 4,842,579 A | 6/1989 | Shiber | |
| 5,041,082 A | 8/1991 | Shiber | |
| 5,047,040 A | 9/1991 | Simpson et al. | |
| 5,125,888 A | 6/1992 | Howard et al. | |

(Continued)

*Primary Examiner*—Michael Peffley
(74) *Attorney, Agent, or Firm*—Harness, Dickey & Pierce, P.L.C.

(57) ABSTRACT

A magnetically navigable catheter includes a sheath having a proximal end and a distal end, and an extension member having a proximal end and a distal end, slidably mounted in the sheath so that the distal end portion of the extension member telescopes from the distal end of the sheath. The distal end portion of the extension member being relatively more flexible than the distal end of the sheath. There may be one or more electrodes on the distal end of the extension member. There is also at least one magnet, and preferably more than one magnet, on the distal end portion of the extension member to allow the distal end of extension member to be oriented by the application of an externally applied magnetic field. The catheter preferably also includes a sleeve, having a proximal end and a distal end, the sleeve being slidably mounted in the sheath so that the distal end portion of the sleeve telescopes from the distal end of the sheath, so that the sleeve can be selectively extended and retracted relative to the sheath, and the extension member can be selectively extended and retracted relative to the sleeve. According to the method of this invention, the distal end of the electrode catheter is introduced into the part of the body where the electrode will be used to contact the specific body structures, and the electrode is moved into contact with the body structure by applying an external magnetic field and selectively telescoping the extension member relative to the sheath to bring the electrode on the distal end of the extension member into contact with the specific body structure.

8 Claims, 3 Drawing Sheets

U.S. PATENT DOCUMENTS

| | | | |
|---|---|---|---|
| 5,287,858 A | 2/1994 | Hammerslag et al. | |
| 5,312,427 A | 5/1994 | Shturman | |
| 5,314,407 A | 5/1994 | Auth et al. | |
| 5,314,438 A | 5/1994 | Shturman | |
| 5,353,807 A | 10/1994 | DeMarco | |
| 5,356,418 A | 10/1994 | Shturman | |
| 5,417,703 A | 5/1995 | Brown et al. | |
| 5,423,838 A | 6/1995 | Willard | |
| 5,429,131 A | 7/1995 | Scheinman et al. | |
| 5,429,136 A | 7/1995 | Milo et al. | |
| 5,501,694 A | 3/1996 | Ressemann et al. | |
| 5,540,707 A | 7/1996 | Ressemann et al. | |
| 5,545,193 A * | 8/1996 | Fleischman et al. | 607/99 |
| 5,554,163 A | 9/1996 | Shturman | |
| 5,776,080 A | 7/1998 | Thome et al. | |
| 5,792,157 A | 8/1998 | Mische et al. | |
| 5,800,428 A | 9/1998 | Nelson et al. | |
| 5,800,497 A | 9/1998 | Bakels et al. | |
| 5,843,153 A | 12/1998 | Johnston et al. | |
| 5,911,720 A * | 6/1999 | Bourne et al. | 606/41 |
| 6,126,647 A | 10/2000 | Posey et al. | |
| 6,129,685 A * | 10/2000 | Howard, III | 600/585 |
| 6,292,678 B1 * | 9/2001 | Hall et al. | 600/374 |
| 6,385,472 B1 | 5/2002 | Hall et al. | |

\* cited by examiner

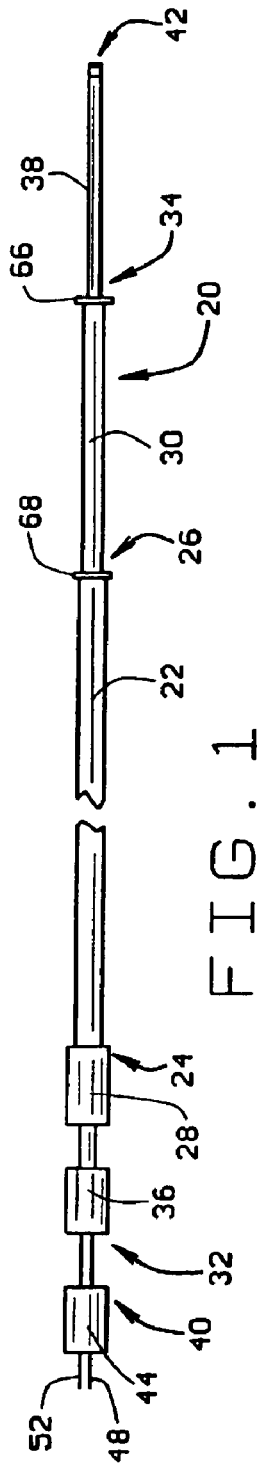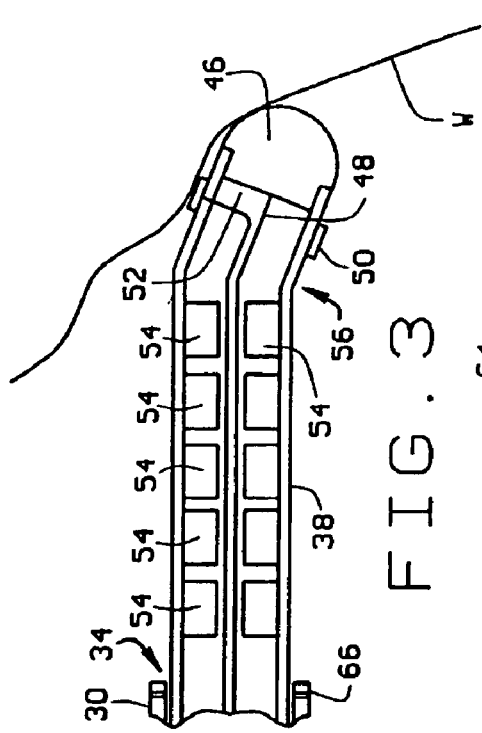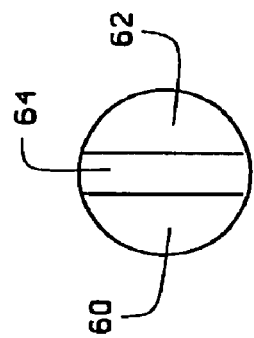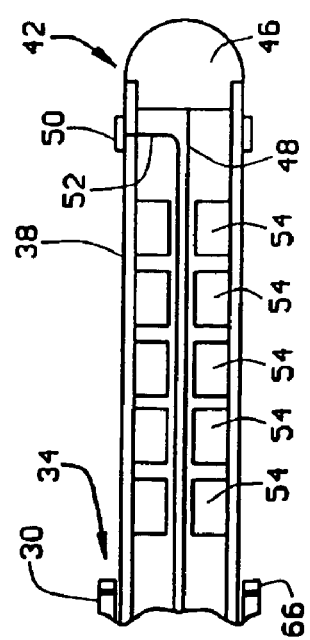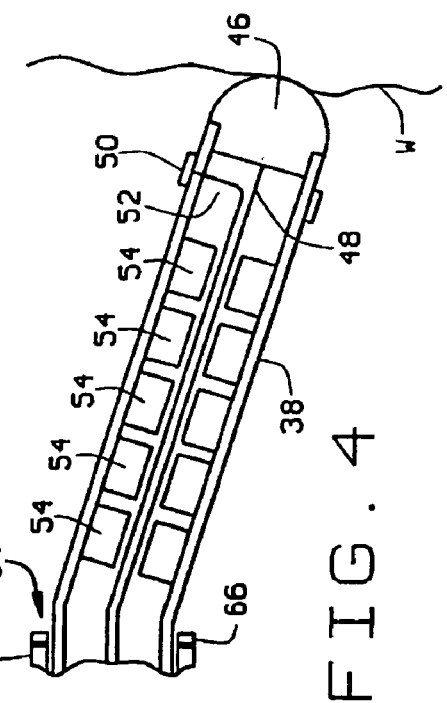

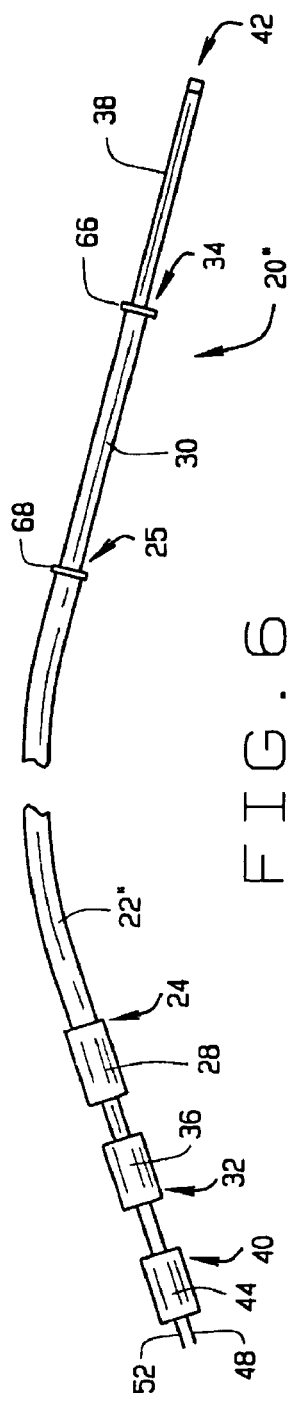
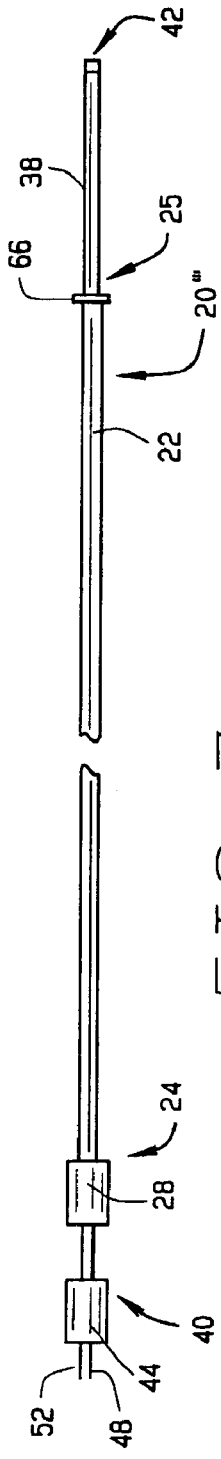
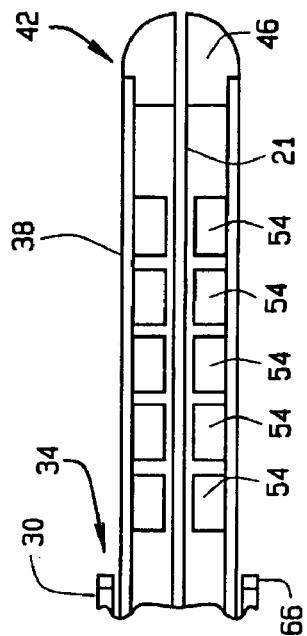
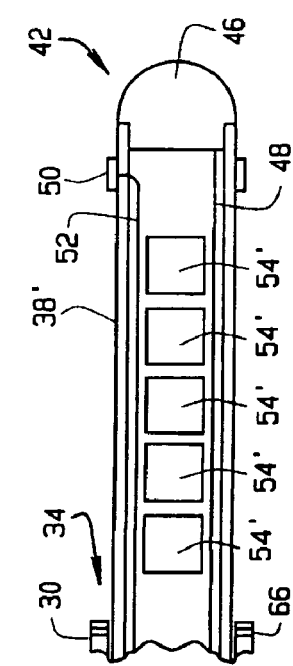
FIG. 6
FIG. 7
FIG. 9
FIG. 8

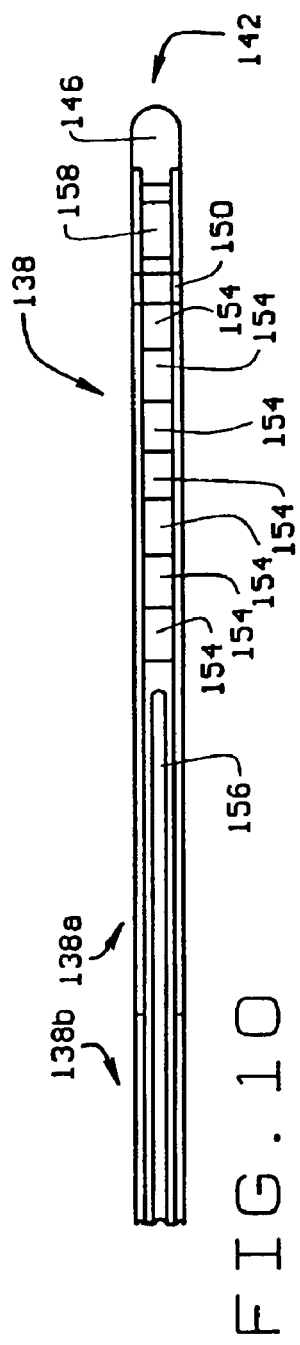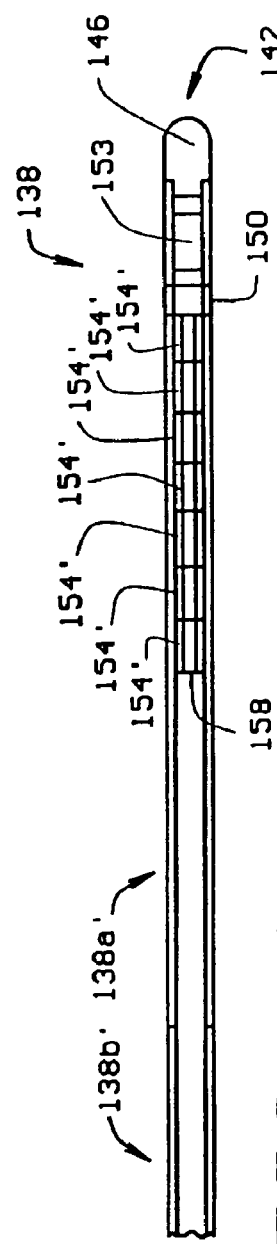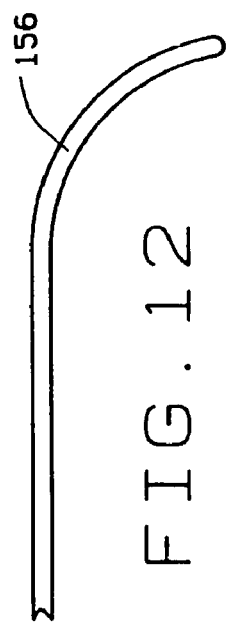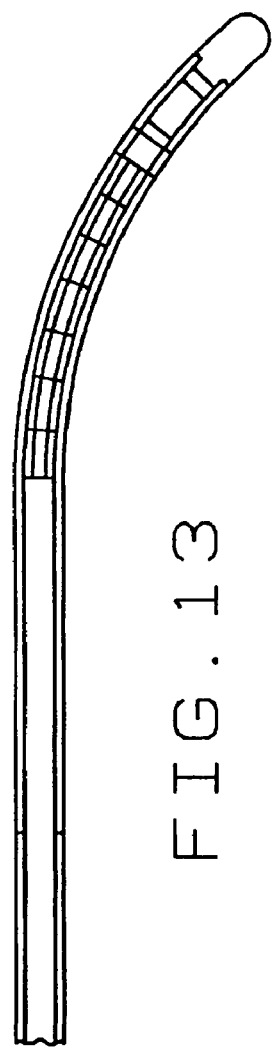
FIG. 10
FIG. 11
FIG. 12
FIG. 13

MAGNETICALLY NAVIGABLE TELESCOPING CATHETER AND METHOD OF NAVIGATING TELESCOPING CATHETER

This application is a continuation application of U.S. patent application Ser. No. 09/999,185, filed Feb. 4, 2002, now abandoned, which is a continuation application of U.S. patent application Ser. No. 09/393,521, filed Sep. 10, 1999, now U.S. Pat. No. 6,385,472, issued May 7, 2002, (incorporated herein by reference).

FIELD OF THE INVENTION

This invention relates to a magnetically navigable telescoping catheter and a method of magnetically navigating a telescoping catheter within open body spaces.

BACKGROUND OF THE INVENTION

Many medical procedures require the ability to accurately navigate medical devices inside the body. In the past, this has been accomplished with mechanically steerable devices. More recently, magnetically navigable medical devices have been developed that can be navigated with an externally applied magnetic field.

However, previously available navigable devices and navigation methods are only marginally acceptable for some procedures where high precision is required. For example, in certain cardiac procedures such as mapping (recording electrical impulses on the surface of the heart); pacing (inducing electrical impulses of the surface of the heart); and ablation (applying RF energy to the heart tissue to ablate the tissue to block stray electrical signals that cause arrhythmias) an electrode must be precisely controlled to contact specific points on the heart. One treatment of cardiac arrhythmias relies upon the formation of a continuous linear lesion from a series of contiguous spot lesions. Such a procedure can be extremely tedious and time consuming with previously available devices and navigation methods.

Examples of mechanically controlled catheters for such procedures include Avitall, U.S. Pat. Nos. 5,354,297, 5,327, 905, and 5,642,736; Webster, U.S. Pat. No. Re 34,502; West et al., U.S. Pat. No. 5,318,525; and Webster, Jr., U.S. Pat. No. 5,626,136. These mechanically actuable catheters typically have a limited number of directions of movement. Moreover to navigate the distal end of the catheter to a particular point, the catheter had to be rotated, but rotation of the proximal end of the catheter did not always directly translate to rotation at the distal end, particularly where the path of the catheter was convoluted. Moreover, twists and turns in the catheter would impair or eliminate the ability to control the distal end of the catheter.

Magnets have also been used in such devices. Scheinman, U.S. Pat. No. 5,429,131 and Grayzel, U.S. Pat. No. 4,809,731. However, not for navigation.

SUMMARY OF THE INVENTION

The present invention relates to a magnetically navigable telescoping catheter, and to a method of navigating such catheter in the body. Generally, the magnetically navigable telescoping catheter of the present invention comprises a sleeve having a proximal end and a distal end. An extension member having a proximal end and a distal end is slidably mounted in the sleeve so that the distal end portion of the extension member telescopes from the distal end of the sleeve. The distal end portion of the extension member is relatively more flexible than the distal end of the sleeve. At least one magnet is positioned on the distal end portion of the extension member to allow the distal end of the extension member to be oriented by the application of an externally applied magnetic field. The position of the distal tip of the catheter can be controlled by the controlled application of a magnetic field to orient the distal end of the extension member, and telescoping the extension member into and out of the sleeve. At least one electrode is positioned on the distal end of the extension member.

In accordance with a preferred embodiment of this invention, a sheath is also provided, and the sleeve is slidably mounted in the sheath so that the distal end of the sleeve can telescope relative to the distal end of the sheath. In navigating the catheter of the preferred embodiment, in addition to the direction control provided by the controlled application of a magnetic field and the telescoping of the extension member relative to the sleeve, the user can also telescope the sleeve relative to the sheath to control the position of the distal end of the extension member. This gives the user a first adjustable length whose direction is controlled by the direction of the magnetic field, and a second adjustable length substantially unaffected by the direction of the magnetic field.

The catheter can be provided with one or more electrodes for cardiac mapping, pacing, or ablation. Alternatively, the catheter can be used in some other procedure such as the delivery of therapeutic agents.

According to the method of this invention, the distal end of the extension member is navigated to the site in the body. Once in the desired location, a magnetic field is applied to orient the distal end portion of the extension member, and the distal end is navigated to a precise location by the relative telescoping of the extension member relative to the sleeve, and in the preferred embodiment also by the relative telescoping of the sleeve relative to the sheath.

With this method, an electrode on the end of the distal end of the extension member can be navigated to contact specific parts of the body, for example the chambers of the heart, to bring an electrode into contact with the tissue for mapping, pacing, or ablation.

The telescoping motion and magnetic guidability of the electrode catheter of the present invention allows superior control of the distal end of the catheter, without regard to the path of the catheter. The improved navigation is both faster, reducing procedure times, and more accurate, allowing the procedures to be successfully completed. However the catheter is of relatively simple and reliable construction. These and other features and advantages will be in part apparent and in part pointed out hereinafter.

BRIEF DESCRIPTION OF THE DRAWINGS

FIG. 1 is a top plan view of a catheter constructed according to the principles of this invention;

FIG. 2 is an enlarged longitudinal cross-sectional view of the extension member; taken along the plane of line 2—2 in FIG. 1;

FIG. 3 is an enlarged longitudinal cross-sectional view of the extension member, showing the flex point on the extension member between the magnets and the electrodes;

FIG. 4 is an enlarged longitudinal cross-sectional view of the extension member, showing the flex point on the extension member between magnets and the distal end of the sleeve;

FIG. 5 is a distal end elevation view of an alternate construction of the catheter, showing an alternate arrangement of the electrodes;

FIG. 6 is a top plan view of an alternate construction of the electrode catheter in which the sheath is curved;

FIG. 7 is a top plan view of an alternate construction of the electrode catheter without a sleeve;

FIG. 8 is longitudinal cross-sectional view of an alternate construction of the extension member;

FIG. 9 is a longitudinal cross-sectional view of an alternative construction of a telescoping catheter;

FIG. 10 is a longitudinal cross-sectional view of an alternate construction of the extension member adapted for use with a stylette;

FIG. 11 is a longitudinal cross-sectional view of an alternate construction of the extension member adapted for use with a stylette;

FIG. 12 is a longitudinal cross-sectional view of a stylette adapted far use with the extension members shown in FIG. 10 or 11; and FIG. 13 is a longitudinal cross-sectional view of a stylette adapted for use with the extension members shown in FIG. 11.

Corresponding reference numerals indicate corresponding parts throughout the several views of the drawings.

DETAILED DESCRIPTION OF THE PREFERRED EMBODIMENT

A catheter constructed according to the principles of the present invention is indicated generally as 20 in FIG. 1. As shown in the figures and described herein, catheter 20 is an electrode catheter having one or more electrodes thereon, but this invention is not so limited and the catheter can be used for other purposes, for example the delivery of diagnostic or therapeutic agents. FIG. 9 shows such a catheter 20' with a central passage 21 for the delivery of diagnostic or therapeutic agents.

The electrode catheter 20 of the preferred embodiment comprises a sheath 22 having a proximal end 24 and a distal end 26. The sheath 22 is preferably about 120 cm long. There is a connector block 28 at the proximal end of the sheath 22. The sheath 22 is preferably made from conventional sheath material, with an outside diameter of about 9 French. As shown in FIG. 6, instead of the straight sheath 22, in an alternate construction of the electrode catheter 20", the sheath 22" may be pre-curved, for example to facilitate a transseptal approach to the left atrium. A sleeve 30 having a proximal end 32 and a distal end 34 is slidably mounted in the sheath 22 so that the distal end portion of the sleeve telescopes from the distal end 26 of the sheath. The sleeve 30 is preferably about 125 cm long. There is a connector block 36 at the proximal end of the sleeve 30. The sleeve 30 is preferably made from a conventional sheath material, with an outside diameter of about 8 French. (In an alternate construction of the electrode catheter 20'" as shown in FIG. 7, there is no sleeve 30.)

An extension member 38, having a proximal end 40 and a distal end 42 is slidably mounted in the sleeve 30 so that the distal end portion of the extension member telescopes from the distal end 34 of the sleeve. There is a connector block 44 at the proximal end of the extension member 38. The extension member 38 is preferably a tube, made from a conventional catheter material, with an external diameter of about 7 French. The extension member is preferably about 130 cm long. The distal end portion of the extension member 38 is generally relatively more flexible than the distal end portion of the sleeve 30. In one alternate construction the entire extension member 38 is flexible. In a second alternate construction, the portion of the extension member containing the magnets (as discussed below) is relatively rigid, while the portion of the extension member just proximal to the magnets is flexible to allow the extension member to flex. At least one electrode is positioned on the distal end of the extension member 38. As shown in FIG. 2, in the preferred embodiment there is a first electrode 46 on the distal end of the extension member 38, having a generally hemispherical shape. This rounded shape facilitates navigation, and prevents damage to the surfaces that the distal end of the extension member contacts. A lead wire 48 extends from the electrode 46, through the extension member 38, to the proximal end 40 of the extension member. A second electrode 50, in the form of an annular band, extends circumferentially around the distal end portion of the extension member 38. A lead wire 52 extends from the electrode 50, through the extension member 38, to the proximal end 40 of the extension member. The lead wires 48 and 52 can be connected to a measuring device to measure electrical potential between the electrodes. Alternatively, the lead wires 48 and 52 can be used to force a current through the tissue for electrical pacing of the heart. Lead wire 48 can also be connected to a source of RF energy to provide such energy to electrode 46 to ablate tissue in contact with the electrode. Additional electrodes, or electrodes in other configurations and arrangements can be provided. For example, in the alternate construction shown in FIG. 5, the distal end 42 of the extension member 38 can be provided with two electrodes 60 and 62, separated and electrically insulated from each other by a generally diametrically extending partition 64.

At least one magnet is positioned on the distal end portion of the extension member 38 to allow the distal end 42 of the extension member to be oriented by the application of an externally applied magnetic field. The externally applied magnetic field may be applied, for example with a magnetic surgery system like that disclosed in co-pending U.S. patent application Ser. No. 08-920,446, filed Aug. 29, 1997, entitled Method and Apparatus for Magnetically Controlling Motion Direction of a Mechanically Pushed Catheter. In this preferred embodiment, there are a plurality of magnets 54 inside the tube forming the extension member 38. Each of the magnets 54 preferably has an annular shape with a central passage through which the lead wires 48 and 52 may pass. As shown in FIG. 8, in an alternate construction of the extension member 38', the magnets 54' are solid with a smaller diameter, allowing wires 48 and 52 to pass between the magnets and the wall of the extension member 38'. The magnets 54 are preferably closely spaced to each other, and may even be touching so that they are held together by mutual magnetic attraction. This configuration maximizes the volume of magnetic material while keeping the extension member 38 flexible. The magnets 54 are spaced proximally from the electrodes 46 and 50 on the distal end of the extension member to form a flex point 56 in the extension member between the magnets and the electrodes. Similarly, the extension member 38 preferably can telescope out of the sleeve 30 beyond the most proximal of the magnets 54 to form a flex point 58 in the extension member between the magnets and the distal end of the sleeve.

The electrodes 46 and 50 and magnets 54 are typically radio-opaque so that the distal end portion of the extension member is visible in real time fluoroscope images. The distal end 34 of the sleeve 30 is preferably provided with a radio-opaque band 66, and the distal end 26 of the sheath 22 is provided with a radio-opaque band 68, so that the distal ends of the sleeve and the shaft are also visible under fluoroscopy. This helps the user navigate the distal end 42 of the extension member into the desired position. The procedure can be viewed in one or more two-dimensional images, or conventional image processing can be used to render a three dimensional view of the device which could then be placed within a three-dimensional image set (e.g., from MRI) of the body portion. The radio-opaque electrodes 46 and 50, magnets 54, and bands 66 and 68 also facilitate automating navigation of the distal end, by providing feedback of the position of the distal ends of the sleeves.

In operation the distal end of the device 20 is navigated to the site in the body where the procedures, such as an atrial mapping, pacing, and ablation, are to occur. The device 20 extends into a heart chamber, for example into the right atrium from the inferior vena cava, into the left atrium from the right atrium via a transseptal puncture, or into the right ventricle via the tricuspid valve or into the left ventricle via the aortic valve. Once the distal end portion of the device is in the chamber, a magnetic field is applied to provide an orienting force to the extension member 38. The magnetic field causes the magnets 54 to align in the selected direction. The electrode on the distal end of the extension member 38 is then manipulated to the desired location by selectively telescoping the sleeve 30 relative to the sheath 22, and the extension member relative to the sleeve. Depending on the navigation system being used, the manipulation could be an iterative process, whereby the navigation system constantly tweaks the direction of the magnetic field, based on the location of the tip of the extension member and the desired target location. It would also be possible to automate the process, allowing the surgeon to input either a desired direction or location, and using a computer to control the magnetic field and the telescoping of the sleeve and the extension member.

In the case of electrophysiologic mapping or pacing, as shown in FIG. 3 the distal end portion of the extension member 38 is urged against the wall W of the chamber to cause the end to flex at flex point 56 proximal of the electrodes 46 and 50 but distal of the magnets 54. This allows both electrodes 46 and 50 to lie against the wall W of the chamber, and allows the measurement of monopolar or bipolar electrical impulses in the wall of the atrium between the electrodes. By carefully navigating the distal end portion of the extension member 38 across the surface of the chamber, the entire cardiac chamber can be electrically mapped.

In the case of therapeutic ablation, as shown in FIG. 4, the electrode 46 on the distal end of the extension member 38 can be precisely navigated along the wall of the atrium, where RF energy can be applied to ablate the underlying tissue. The precise navigational control permitted by the electrode catheter allows both focal lesions and the creation of lines of continuous lesions to be formed in the chamber, blocking the path of stray electrical signals that cause the arrhythmia. Such continuous lines of lesions were extremely difficult, if not impossible to form, particularly in the left atrium, with prior mechanically steerable catheters.

An alternate construction of the extension member 38 is indicated generally as 138 in FIG. 10. Extension member 138, having a proximal end and a distal end 142 is slidably mounted in a sleeve (not shown) so that the distal end portion of the extension member telescopes from the distal end of the sleeve. The extension member 138 is preferably a tube made from a conventional catheter material with an external diameter of about 7 French. The extension member is preferably about 130 cm long the tube preferably comprises sections of different stiffness to facilitate navigation of the catheter. In the preferred embodiment, the distal section 138*a* is made from a very flexible vinyl or polyethylene or polyurethane, and the proximal section 138*b* is made from a relatively stiffer material such as nylon. There is a first electrode 146 on the distal end of the extension member 138, having a generally hemispherical. This rounded shape facilitates navigation, and prevents damage to the surfaces that the distal end of the extension member contacts. A lead wire extends from the electrode 146, through the extension member 138, to the proximal end of the extension member. A second electrode 150, in the form of an annular band, extends circumferentially around the distal end portion of the extension member 138. A lead wire extends from the electrode 150, through the extension member 138, to the proximal end of the extension member. The lead wires can be connected to a measuring device to measure electrical potential between the electrodes. Alternatively the lead wires can be used to force a current through the tissue for electrical pacing of the heart. The lead wires can also be connected to a source of RF energy to provide such energy to the electrodes to ablate tissue in contact with the electrodes. Additional electrodes, or electrodes in other configurations and arrangements can be provided.

A localization device 153 is preferably incorporated into the extension member 138 so that the location of the extension member, and preferably both the location and orientation of the extension member, can be determined. In the preferred embodiment, the localization is a magnet device, such as a triaxial coil receiver for AC electromagnetic fields, but the localization could be done with some other device, such as ultrasound devices.

A plurality of magnets 154 are positioned on the distal end portion of the extension member 138 to allow the distal end 142 of the extension member to be oriented by the application of an externally applied magnetic field. The tube forming the extension member 138 is open proximal to the magnets to receive at the distal end of the stylette 156 to stiffen, shape, or guide the distal end of the extension member. The stylette 156 is inserted into the proximal end of extension member 138 and advanced to the distal end where the stylette in the lumen of the tube forming the extension member selectively stiffens the extension member and/or shapes the extension member to facilitate navigation. The distal end of the stylette can be preformed for a particular navigation and inserted into the extension member 138 to shape the extension member for the navigation. The stylette can also be used to push the extension member. The stylette can be selectively inserted and removed to selectively temporarily stiffen and temporarily soften the distal end of the extension member to facilitate navigation.

An alternate construction of the extension member 138 is indicated generally as 138' in FIG. 11. Extension member 138' is similar in construction to extension member 138, and corresponding parts are identified with corresponding reference numerals. However, rather than cylindrical magnets 154, extension member 138' has annular magnets 154', whose central opening are aligned to form a passage 158 for the stylette 156. The stylette 156 can be inserted through the proximal end of extension member 138' and into the passage 158 to selectively stiffen and/or shape the distal portion of the extension member 138. As shown in FIG. 12, the distal end portion of the stylette can be bent, and as shown in FIG. 13 it can be inserted into the extension member 138' to shape the distal end of the extension member. The passage 158 also allow the stylette 156 to apply a pushing force closer to the distal end of the extension member.

The movement of the sheath, the extension member, and even the stylette, can be automated and operated by motor instead of manually, if desired.

What is claimed is:

1. A method of mapping the electrical characteristics of the left atrium of the heart comprising:
   providing a magnetically navigable electrode catheter comprising a sleeve having a proximal end and a distal end, an extension member having a proximal end and a distal end, the extension member being slidably mounted in the sleeve so that the distal end portion telescopes from the distal end of the sleeve, the distal end portion of the extension member being relatively more flexible than the distal end of the sleeve;
   providing at least one electrode on the distal end of the extension member; and at least one magnet on the distal end of portion of the extension member, wherein the distal end portion of the extension member containing the at least one magnet is relatively rigid and the portion of the extension member just proximal to the at least one magnet is flexible;
   introducing the distal end of the magnetically navigable electrode catheter into left atrium;
   moving the electrode into contact with a selected point on the surface of the left atrium by applying an external magnetic field, such that the catheter bends at a point proximal to the distal end portion having the at least one magnet, and selectively telescoping extension member relative to the sleeve to bring the electrode on the distal end of the extension member into contact with the specific point on the surface of the left atrium;
   measuring the electrical characteristics of the left atrium between the electrodes.

2. The method according to claim 1 wherein the magnetically navigable electrode catheter further comprises a sheath having a proximal end and a distal end, the sleeve being slidably mounted in the sheath so that the distal end portion of the sleeve telescopes from the distal end of the sheath, and wherein the step of moving the electrode into contact with a selected point on the surface of the left atrium includes selectively telescoping the sleeve relative to the sheath.

3. The method according to claim 1 wherein the extension member has a lumen extending at least partly therethrough, the method comprising inserting a stylette into the lumen in the extension member to stiffen the extension member.

4. The method according to claim 1 wherein the extension member has a lumen extending at least partly therethrough, the method comprising inserting a pre-shaped stylette into the lumen in the extension member to shape the extension member to facilitate navigation of the extension member.

5. The method according to claim 1 wherein the extension member has a lumen extending at least partly therethrough, the method comprising inserting a stylette into the lumen in the extension member and pushing the stylette to push the extension member.

6. A method of therapeutically ablating tissue in the left atrium of the heart comprising:
   providing a magnetically navigable electrode catheter comprising a sleeve having a proximal end and a distal end, an extension member having a proximal end and a distal end, the extension member being slidably mounted in the sleeve so that the distal end portion telescopes from the distal end of the sleeve, the distal end portion of the extension member being relatively more flexible than the distal end of the sleeve;
   providing at least one electrode on the distal end of the extension member; and at least one magnet on the distal end portion of the extension member;
   introducing the distal end of the magnetically navigable electrode catheter into left atrium;
   moving the electrode into contact with a selected point on the surface of the left atrium by applying an external magnetic field and selectively telescoping extension member relative to the sleeve to bring the electrode on the distal end of the extension member into contact with the specific point on the surface of the left atrium; and
   applying an RF signal to the tissue in contact with the electrode to ablate the tissue, wherein the extension member has a lumen extending at least partly therethrough, the method comprising inserting a stylette into the lumen in the extension member to stiffen the extension member.

7. A method of therapeutically ablating tissue in the left atrium of the heart comprising:
   providing a magnetically navigable electrode catheter comprising a sleeve having a proximal end and a distal end, an extension member having a proximal end and a distal end, the extension member being slidably mounted in the sleeve so that the distal end portion telescopes from the distal end of the sleeve, the distal end portion of the extension member being relatively more flexible than the distal end of the sleeve;
   providing at least one electrode on the distal end of the extension member; and at least one magnet on the distal end portion of the extension member;
   introducing the distal end of the magnetically navigable electrode catheter into left atrium;
   moving the electrode into contact with a selected point on the surface of the left atrium by applying an external magnetic field and selectively telescoping extension member relative to the sleeve to bring the electrode on the distal end of the extension member into contact with the specific point on the surface of the left atrium; and
   applying an RF signal to the tissue in contact with the electrode to ablate the tissue, wherein the extension member has a lumen extending at least partly therethrough, the method comprising inserting a pre-shaped stylette into the lumen in the extension member to shape the extension member to facilitate navigation of the extension member.

8. A method of therapeutically ablating tissue in the left atrium of the heart comprising:
   providing a magnetically navigable electrode catheter comprising a sleeve having a proximal end and a distal end, an extension member having a proximal end and a distal end, the extension member being slidably mounted in the sleeve so that the distal end portion telescopes from the distal end of the sleeve, the distal end portion of the extension member being relatively more flexible than the distal end of the sleeve;
   providing at least one electrode on the distal end of the extension member; and at least one magnet on the distal end portion of the extension member;
   introducing the distal end of the magnetically navigable electrode catheter into left atrium;
   moving the electrode into contact with a selected point on the surface of the left atrium by applying an external magnetic field and selectively telescoping extension member relative to the sleeve to bring the electrode on the distal end of the extension member into contact with the specific point on the surface of the left atrium; and applying an RF signal to the tissue in contact with the electrode to ablate the tissue, wherein the extension member has a lumen extending at least partly therethrough, the method comprising inserting a stylette into the lumen in the extension member and pushing the stylette to push the extension member.

* * * * *